US012635933B2

(12) United States Patent
Shrivastav et al.

(10) Patent No.: US 12,635,933 B2
(45) Date of Patent: May 26, 2026

(54) DETECTION OF PATIENT SEIZURES FOR WEARABLE DEVICES

(71) Applicant: Medtronic, Inc., Minneapolis, MN (US)

(72) Inventors: Maneesh Shrivastav, Blaine, MN (US); PavanKumar Ithapu, Hyderabad (IN)

(73) Assignee: Medtronic, Inc., Minneapolis, MN (US)

( * ) Notice: Subject to any disclaimer, the term of this patent is extended or adjusted under 35 U.S.C. 154(b) by 275 days.

(21) Appl. No.: 18/289,223

(22) PCT Filed: Apr. 29, 2022

(86) PCT No.: PCT/US2022/026997
§ 371 (c)(1),
(2) Date: Nov. 1, 2023

(87) PCT Pub. No.: WO2022/235512
PCT Pub. Date: Nov. 10, 2022

(65) Prior Publication Data
US 2024/0366142 A1 Nov. 7, 2024

Related U.S. Application Data

(60) Provisional application No. 63/182,878, filed on May 1, 2021.

(51) Int. Cl.
*A61B 5/374* (2021.01)
*A61B 5/00* (2006.01)
(Continued)

(52) U.S. Cl.
CPC .......... *A61B 5/4094* (2013.01); *A61B 5/1117* (2013.01); *A61B 5/374* (2021.01);
(Continued)

(58) Field of Classification Search
CPC ....... A61B 5/1117; A61B 5/256; A61B 5/374; A61B 5/4064; A61B 5/4094;
(Continued)

(56) References Cited

U.S. PATENT DOCUMENTS 9,538,950 B1   1/2017  Bibian et al.
2011/0218454 A1   9/2011  Low
(Continued)

FOREIGN PATENT DOCUMENTS

WO   WO 2020/223354 A1   11/2020

OTHER PUBLICATIONS

Ozmen et al., "A Biologically Inspired Approach to Frequency Domain Feature Extraction for EEG Classification," Hindawi, Computational and Methematical Methods in Medicine, vol. 2018, Article ID 9890132, 10 pages.
(Continued)

*Primary Examiner* — George Manuel
(74) *Attorney, Agent, or Firm* — Husch Blackwell LLP

(57) ABSTRACT
Systems and method for seizure detection. A seizure detection device utilizes frequency discrimination, time series features, and machine learning clustering algorithms to distinguish between the EEG signal of those experiencing a seizure compared to those who are not experiencing a seizure.

20 Claims, 10 Drawing Sheets

Comparison of EEG Bands

Gamma: 30-100+ Hz

High frequency waves.
Simultaneous info processing.

Beta: 12-30 Hz

Normal waking state.
Problem solving.

Alpha: 8-12 Hz

Resting state.
Mental coordination.

Theta: 4-7 Hz

Deep meditation.
Learning, memory, intuition.

Delta: 0-4 Hz

Deep meditation, dreamless sleep

(51) Int. Cl.
  *A61B 5/11*       (2006.01)
  *G16H 40/67*      (2018.01)
  *G16H 50/20*      (2018.01)
(52) U.S. Cl.
  CPC .......... *A61B 5/6831* (2013.01); *A61B 5/6833*
        (2013.01); *A61B 5/746* (2013.01); *G16H*
        *40/67* (2018.01); *G16H 50/20* (2018.01)
(58) Field of Classification Search
  CPC ................ A61B 5/6831; A61B 5/6833; A61B
        5/7267; A61B 5/746; G16H 40/67; G16H
                                        50/20
  See application file for complete search history.

(56)                References Cited

U.S. PATENT DOCUMENTS

| | | | |
|---|---|---|---|
| 2012/0245481 A1* | 9/2012 | Blanco ................. | A61B 5/4094 |
| | | | 600/544 |
| 2013/0209435 A1 | 8/2013 | Dudley et al. | |
| 2016/0235324 A1 | 8/2016 | Mershin et al. | |
| 2017/0140115 A1 | 5/2017 | Ma et al. | |
| 2017/0262596 A1 | 9/2017 | Sengupta et al. | |

OTHER PUBLICATIONS

Yaeger et al., "United States regulatory approval of medical devices and software applications enhanced by artificial intelligence," Fellowship of Postgraduate Medicine, Published by Elsevier Ltd., 2019, 6 pages.
Erani et al., "Abstract TP314: EEG Has High Precision for Diagnosing Stroke Hours After Onset," Stroke, vol. 50, Issue Suppl_1, Feb. 2019, 2 pages.

Cook et al., "Prediction of seizure likelihood with a long-term, implanted seizre advisory system in patients with drug-resistant epilepsy: a first-in-man study," Lancet Neurol. Jun. 2013, 3 pages.
Fisher et al., "Seizure diaries for clinical research and practice: limitations and future prospects," Epilepsy Behav. Jul. 2012, 3 pages.
Finnigan et al., "EEG in ischaemic stroke: Quantitative EEG can uniquely inform (sub-)acute prognoses and clinical management," Clinical Neurophysiology 124 (2013) 10-19.
Swanson et al., "Epilepsy, Functional Neurosurgery, and Pain," Operative Neurosurgery, vol. 17, Issue Supplemental 1, Aug. 2019, pp. S209-S228.
Poomipat Boonyakitanont et al., "A review of feature extraction and performance evaluation in epileptic seizure detection using EEG," arxiv.org, Cornell University Library, 201 Olin Library Cornell University Ithaca, NY 14853, Aug. 1, 2019, XP081453743.
PCT/US2022/026997, Search Report and Written Opinion dated Aug. 11, 2022, 19 pages.
Zhang et al., "Personalized Prediction Model for Seizure-Free Epilepsy with Levetiracetam Therapy: A Retrospective Data Analysis Using Support Vector Machine," Br J Clin Pharmacol, Jul. 2018, doi: 10.1111/bcp.13720, 10 pages.
Sadaye et al., "Epileptic Seizure Prediction Using Power Spectrum and Amplitude Analysis of Beta Band of EEG Signals," International Journal of Computer Applications (0975-8887), vol. 155, No. 9, Dec. 2016, 5 pages.
Zhao et al., "Seizure Detection: Do Current Devices Work? And When Can They be Useful?," Current Neurology and Neuroscience Reports, 2018, 19 pages.
Kusmakar et al., "Gaussian Mixture Model for the Identification of Psychogenic Non-Epileptic Seizures Using a Wearable Accelerometer Sensor," Conf Proc IEEE Eng Med Biol Soc., 2016, 4 pages.
Doria, "Incidence, Implications, and Management of Seizures Following Ischemic and Hemorrhagic Stroke," Current Neurology and Neuroscience Reports, 19(37), May 2019, 8 pages.

\* cited by examiner

102

Descriptive Statistics

|  | No Seizure | Seizure Present |
|---|---|---|
| Mean | 77858 | 10950 |
| Median | 77121 | 8340 |
| Mean absolute deviation | 6164 | 16977 |
| Standard deviation | 7714 | 20869 |
| Skewness | -0.5126 | -0.3745 |
| Kurtosis | 2.79 | 2.58 |

Comparison of EEG Bands

Gamma: 30-100+ Hz

High frequency waves.
Simultaneous info processing.

Beta: 12-30 Hz

Normal waking state.
Problem solving.

Alpha: 8-12 Hz

Resting state.
Mental coordination.

Theta: 4-7 Hz

Deep meditation.
Learning, memory, intuition.

Delta: 0-4 Hz

Deep meditation, dreamless sleep

DETECTION OF PATIENT SEIZURES FOR WEARABLE DEVICES

FIELD

The present technology is generally related to medical devices and, more particularly, to systems and methods for detecting patient conditions.

BACKGROUND

Some neurological disorders, such as epilepsy, are characterized by the occurrence of seizures. Epilepsy affects 1-2% of the population, and 25-30% of those with epilepsy continue to suffer seizures.

Seizures may be attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which may result in progressive loss of brain function over time.

Today, a significant number of daytime and nighttime seizures are still missed; it is estimated that 30-50% of daytime seizures and 86% of nighttime seizures are missed. The quest for highly accurate seizure detection has been a highly desirable goal for the treatment of those who suffer from epilepsy.

Traditional signal processing techniques and other published classification schemes can achieve up to 91% detection accuracy. Often, such techniques require the patient to wear intrusive sensors, such as a high-density scalp electroencephalogram (EEG) array having many electrodes. Such sensors can interfere with patient movement and daily activities, making them impractical for prolonged monitoring.

Therefore, there is a need for improved systems and methods for seizure detection.

SUMMARY

The techniques of this disclosure generally relate to medical devices implementing a predictive algorithm based on machine learning techniques and historical patient EEG information to classify EEGs into seizure and non-seizure categories. A supervised algorithm utilizing a support vector machine can produce reproducible classification results with as high as 97% detection accuracy, exceeding performance of traditional classification schemes.

Embodiments described herein present a new way to classify seizures with predictive analytics instead of just traditional signal processing techniques. Further, embodiments can utilize small epochs of data, thereby including very fast learning algorithms for seizure detection. Additionally, embodiments can utilize less invasive sensors (e.g. on wearable devices) than traditional detection techniques.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Subject matter hereof may be more completely understood in consideration of the following detailed description of various embodiments in connection with the accompanying figures, in which.

Figure 1A:
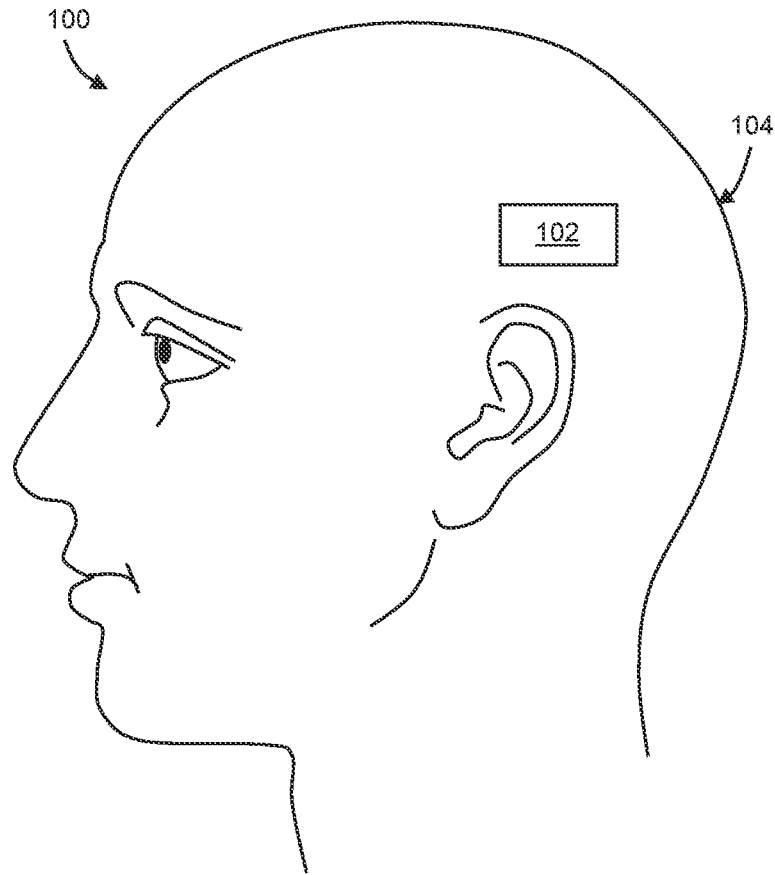
FIG. 1A is a block diagram of a system configured to detect a medical condition in accordance with examples of the present disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Embodiments described herein utilize frequency discrimination, time series features, digital signal processing techniques, and machine learning clustering algorithms to distinguish between the EEG signal of those experiencing a seizure compared to those who are not experiencing a seizure.

Referring to FIG. 1A, a block diagram of a system 100 configured to detect a medical condition is depicted, in accordance with examples of the present disclosure.

System 100 generally comprises detection device 102 positioned proximate a patient 104. As illustrated, detection device 102 is configured to sense electrical signals from a region near or on the patient's head, such as the frontal region, parietal region, occipital region, temporal region, auricular region, mastoid region, facial region, orbital region, infraorbital region, nasal region, zygomatic region, zuccal region, parotid region, oral region, and/or mental region.

In particular, detection device 102 can be positioned adjacent a rear portion of the patient's neck or base the patient's skull or near the patient's temple. In embodiments, detection device 102 can utilize a subcutaneous technique or application on the dermal layer. For example, in the aforementioned positions, implantation under the patient's skin is relatively simple. In embodiments, temporary application of a wearable sensor device on the skin of patient 104 (e.g., coupled to a bandage, garment, band, or adhesive member) does not unduly interfere with patient movement and activity. For example, detection device 102 can be operably coupled to the skin of patient 104 by an adhesive element. Detection device 102 can be integrated into or comprise a headband-type wearable for operably coupling to the skin of patient 104. Detection device 102 is configured with a resident algorithm to determine a seizure based on the sensed electrical signals.

Figure 1B:
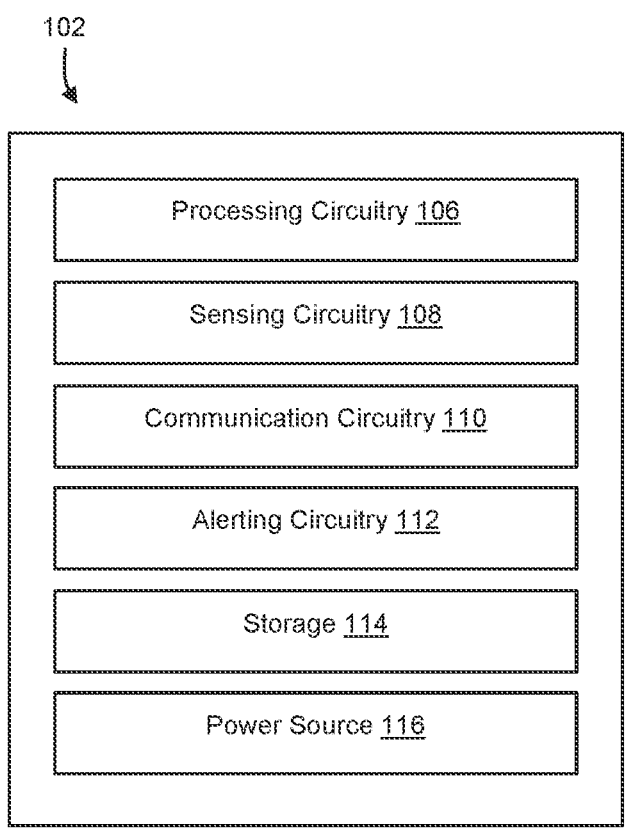
FIG. 1B is a further block diagram of the system of FIG. 1A in accordance with examples of the present disclosure.

Referring to FIG. 1B, a further block diagram of the system of FIG. 1A is depicted, in accordance with examples of the present disclosure. Detection device 102 generally comprises processing circuity 106, sensing circuitry 108, communication circuity 110, alerting circuity 112, storage 114, and power source 116. The components of detection device 102 can be operably coupled as will described and as will be readily understood by one of ordinary skill in the art.

Processing circuitry 106 can include fixed function circuitry and/or programmable processing circuitry. Processing circuitry 110 can include any one or more of a microprocessor, a controller, a DSP, an ASIC, an FPGA, or equivalent discrete or analog logic circuitry. In some examples, processing circuitry 110 can include multiple components, such as any combination of one or more microprocessors, one or more controllers, one or more DSPs, one or more ASICs, or one or more FPGAs, as well as other discrete or integrated logic circuitry. The functions attributed to processing circuitry 110 herein may be embodied as software, firmware, hardware or any combination thereof.

Sensing circuitry 108 is configured to sense electrical activity from the brain and/or heart of patient 104. Accordingly, sensing circuitry 108 can include or can be operable with one or more electrodes. For example, brain stim leads, bands, or any lead electrode can be utilized. In embodiments, a small group of electrodes can be utilized such as on a patch. More particularly, sensing circuitry 108 does not require a high density electrode array.

In an embodiment, sensing circuitry 108 can comprise cortical electrodes and/or band electrodes (i.e. a headband type of device) with multi electrodes separated by a non-conductive element, thereby simulating a multi-electrode array.

Sensing circuitry 108 can be configured to sense brain electrical activity and/or heart electrical activity signals, as well as other signals such as impedance signals for respiration, skin impedance, and perfusion, in some examples. Moreover, sensing circuitry 108 can additionally or alternatively include one or more optical sensors, accelerometers or other motion sensors, temperature sensors, chemical sensors, light sensors, pressure sensors, and acoustic sensors, in some examples. In embodiments, sensing circuitry 108 can include one or more filters and amplifiers for filtering and amplifying signals received from one or more of electrodes. In embodiments, sensing circuitry 108 is configured to sample at a frequency that is current-drain efficient. The embodiment is robust and does not rely on bandpass, low pass, or high pass sampling.

Accordingly, embodiments of the sensed data operate on relatively "less" data and/or "less" pre-processing than traditional solutions. Embodiments do not require bandpass filtering. Further, embodiments can make determinations based on very limited data (e.g. one second of data). Embodiments can be sampled with external low density electrodes that circumvents a shower-cap like multi-electrode array. Embodiments can be implemented via an implantable electrode array (i.e. not hundreds of external electrodes). Further, embodiments are compatible with a wireless sensing array or other arrangements to collect brain EEG signals.

Communication circuity 110 can include any suitable hardware, firmware, software, or any combination thereof for communicating with another device. Under the control of processing circuitry 106, communication circuitry 110 can receive downlink telemetry from, as well as send uplink telemetry to one or more external devices using an internal or external antenna. In addition, communication circuity 110 can facilitate communication with a networked computing device and/or a computer network.

Alerting circuitry 112 can include any suitable hardware, firmware, software, or any combination thereof for alerting the user (such as the device-wearing patient 104) or others of a detected seizure. For example, under the control of processing circuitry 106, alerting circuitry 112 can generate an audible sound, vibration, or other notification. In embodiments, alerting circuity 112, via communication circuity 110 can alert by electronically communicating with another device. For example, alerting circuity 112, via communication circuity 110 can send a text message, email, or other electronic communication to one or more devices such as a networked computing device or over a computer network to other external devices.

Storage 114 can comprise a memory and include computer-readable instructions that, when executed by processing circuitry 106, cause sensing circuitry 108, communication circuity 110, and/or alerting circuity 112 to perform various functions attributed to detection device 102. Storage 114 can include can volatile, non-volatile, magnetic, optical, or electrical media, such as a random access memory (RAM), read-only memory (ROM), non-volatile RAM (NVRAM), electrically-erasable programmable ROM (EE-PROM), flash memory, or any other digital media. Storage 114 can also store data generated by sensing circuitry 108, such as signals, or data generated by processing circuitry 106. Storage 114 can include cloud-based storage.

Power source 116 is configured to deliver operating power to the components of detection device 102. Power source 116 can include a battery and a power generation circuit to produce the operating power. In some examples, the battery is rechargeable to allow extended operation. In some examples, recharging is accomplished through proximal inductive interaction between an external charger and an inductive charging coil. Power source 116 can include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 2:
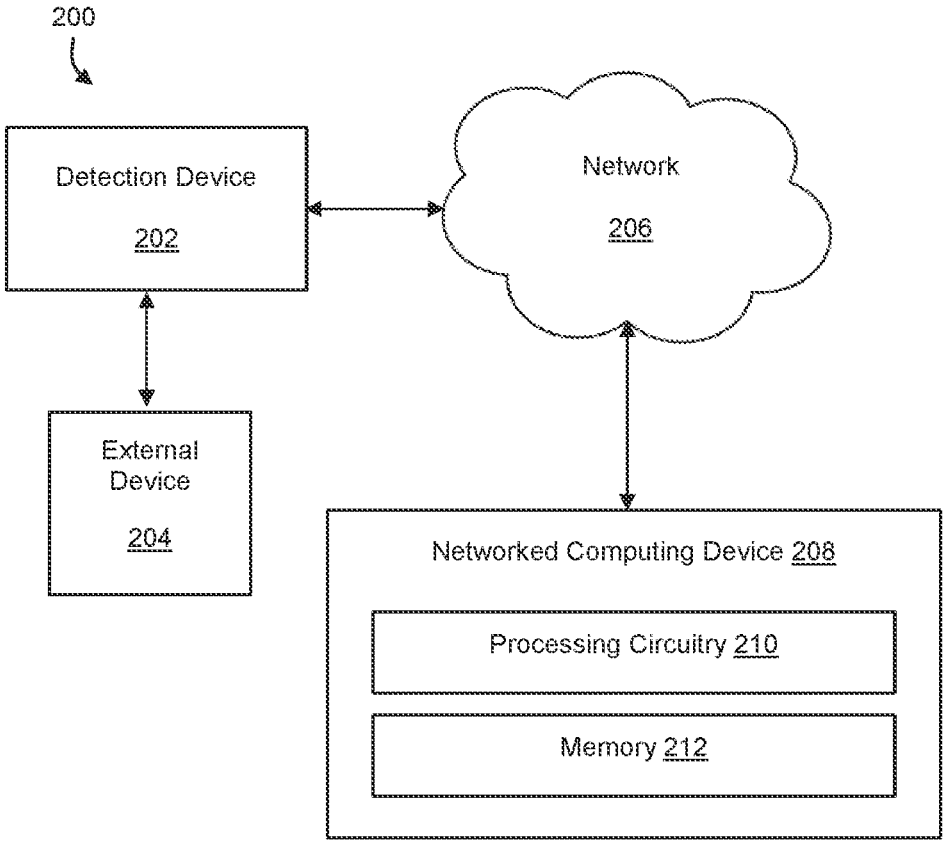
FIG. 2 is a block diagram of another system configured to detect a medical condition in accordance with examples of the present disclosure.

Referring to FIG. 2, a block diagram of another system 200 configured to detect a medical condition is depicted, in accordance with examples of the present disclosure. System

200 generally comprises detection device 202, external device 204, network 206, and networked computing device 208. However, any of external device 204, network 206, or networked computing device 208 can be optional in system 200. For example, in an embodiment, system 200 can comprise detection device 202 and external detection device 202. In another embodiment, system 200 can comprise detection device 202, network 206, and networked computing device 208. In other embodiments, system 200 can comprise detection device 202 and network 206 for operable coupling to other networked devices.

For ease of explanation, detection device 202 is labeled separately from previously-described detection device 102, but one of ordinary skill in the art will readily understand that detection device 202 can be substantially similar to detection device 102 as depicted and described in FIGS. 1A-1B. Differences are described herein.

With reference to external device 204, network 206, and networked computing device 208, embodiments of and the corresponding methods of configuring and operating system 200. can be performed in cloud computing, client-server, or other networked environment, or any combination thereof. The components of the system can be located in a singular "cloud" or network, or spread among many clouds or networks. End-user knowledge of the physical location and configuration of components of the system is not required.

External device 204 is configured to communicate with any detection device, such as detection device 202. Though not depicted, external detection device 202 can comprise processing circuitry, communication circuitry, storage, a user interface, and a power source. External device 204 can be a desktop computer, laptop computer, mobile phone, personal digital assistant, or other suitable device configured for communicating with detection device 202. In some embodiments, external device 204 can be directly connected via wired or wireless connection to detection device 202. In other embodiments (not shown), external device 204 can be connected via network 206. External device 204 is generally configured to receive downlink telemetry from, as well as send uplink telemetry to, detection device 202, or another device.

In embodiments, external device 204 can be configured to log or store data received from detection device 202. For example, data exchanged between external device 204 and detection device 202 can include operational parameters. External device 204 can transmit data including computer readable instructions which, when implemented by detection device 202, can control detection device 202 to export collected data. For example, external device 204 can transmit an instruction to detection device 202 which requests detection device 202 to export collected data (e.g., data corresponding to one or more of the sensed signals, parameter values determined based on the signals, or indications that a condition has been detected, predicted, or classified) to external device 204. In turn, external device 204 can receive the collected data from detection device 202 and store the collected data in external device 204 storage. In embodiments, external device 204 is further configured to communicate with detection device 202 to program or reprogram detection device 202 via different operational parameters or computer readable instructions executable by detection device 202.

Further, external device 204 is configured to display data received from detection device 202, related to detection device 202, or related to system 200. Accordingly, a clinician or patient 104 can interact with external device 204 through a user interface. The user interface can include a display such as an LCD or LED display or other type of screen to present, for example, seizure metrics. The user interface can include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces and provide input. In other examples, the user interface can include audio circuitry for providing audible notifications, instructions or other sounds to patient 104, receiving voice commands from patient 104, or both. In further embodiments, external device 204 is configured to alert a user of a seizure such as in combination with alerting circuitry 112 such as by appropriate external device 204 notifications.

Network 206 comprises a communication network for connecting detection device 202 with other devices (e.g. a wireless communication network, a wired communication network, a cellular communication network, the Internet, a short-range radio network (e.g., via Bluetooth)).

Networked computing device 208 is an additional external device configured to communicate with any sensor device, such as detection device 202 via network 206.

In an embodiment, networked computing device 208 includes processing circuitry 210 and memory 212. Of course, one of skill in the art will appreciate that networked computing device 208 can further comprise communication circuitry, a user interface, and a power source (not shown).

Processing circuitry 210 can include one or more processors that are configured to implement functionality and/or process instructions for execution within networked computing device 208. For example, processing circuitry 210 can be capable of processing instructions stored in memory 212. Processing circuitry 210 can include, for example, microprocessors, DSPs, ASICs, FPGAs, or equivalent discrete or integrated logic circuitry, or a combination of any of the foregoing devices or circuitry. Accordingly, processing circuitry 210 can include any suitable structure, whether in hardware, software, firmware, or any combination thereof, to perform the functions ascribed herein to processing circuitry 210.

Memory 212 can be configured to store information within networked computing device 208 during operation. Memory 212 can include a computer-readable storage medium or computer-readable storage device. In some examples, memory 212 includes one or more of a short-term memory or a long-term memory. Memory 212 can include, for example, RAM. dynamic random access memories (DRAM), static random access memories (SRAM), magnetic discs, optical discs, flash memories, or forms of electrically programmable memories (EPROM) or EEPROM. In some examples, memory 212 is used to store data indicative of instructions for execution by processing circuitry 210. Memory 212 can be used by software or applications running on external networked computing device 208 to temporarily store information during program execution.

In contrast to device 102, which does not have access to external computing power and can be utilized in an ambulatory or emergency setting, detection device 202 has access to external computing power and can be utilized in a clinical setting. In particular, networked computing device 208 is configured to receive data from detection device 202 and at least partially assist in the analysis to determine a seizure. For example, detection device 202 can utilize additional electrodes or higher sampling and thus utilize networked computing device 208 for data analysis at a relatively higher density.

Figure 3:
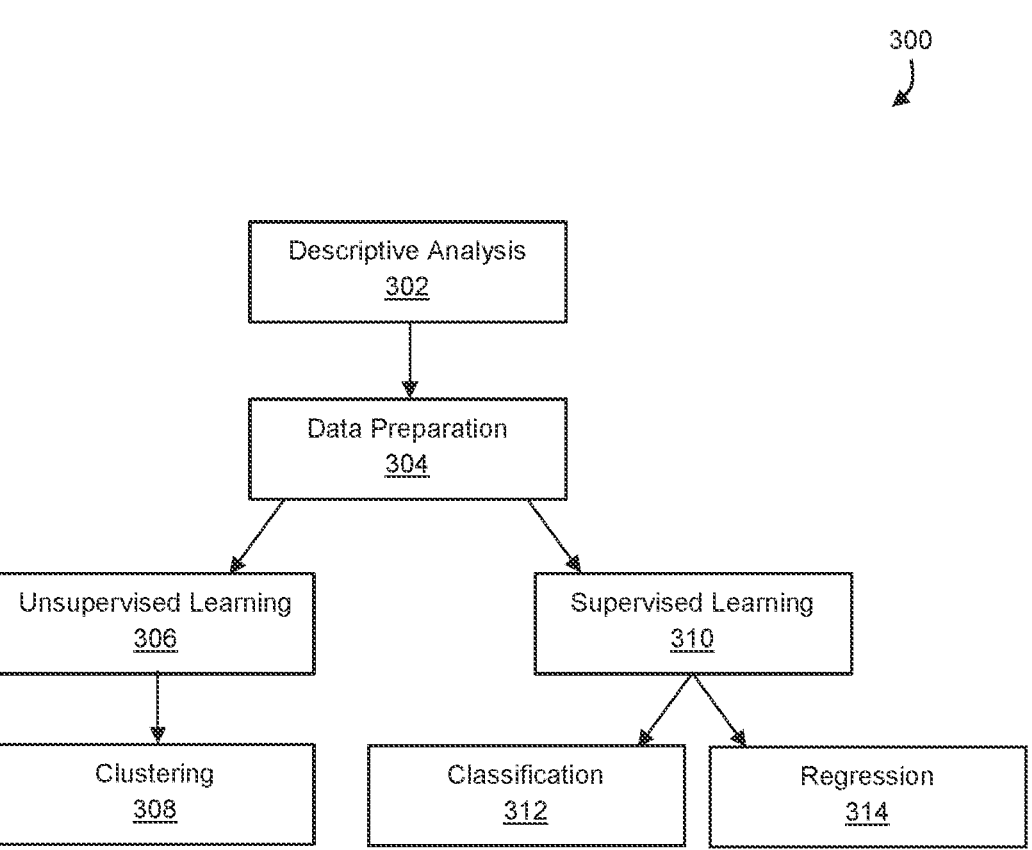
FIG. 3 is a flowchart illustrating an example method for analyzing seizure data in accordance with examples of the present disclosure.

Referring to FIG. 3, a flowchart illustrating an example method 300 for analyzing seizure data in accordance with examples of the present disclosure. As will be readily understood by one of skill in the art, the techniques and sub-techniques described herein with respect to FIG. 3 can be applied for pre-processing seizure data to define the features and algorithms to be subsequently executed by a detection device. Moreover, the techniques and sub-techniques described herein with respect to FIG. 3 can be applied to active seizure detection processing.

In an embodiment, method 300 can be applied to a database of seizure data in generating the features and algorithms utilized by a detection device for seizure detection. Embodiments can be recursive or iterative and learn from previous iterations. In embodiments, each of the components described herein can be recursive or iterative, or entire method 300 can be recursive or iterative.

For example, referring again to FIG. 2, networked computing device 208 can include or be communicatively coupled with an existing database of seizure data. Networked computing device 208 can accordingly be utilized to define seizure detection features and algorithms definition via method 300 and implementation using processing circuity 210. Once defined, networked computing device 208 can communicate over network 206 to program the components of detection device 202.

In another embodiment, detection device 202 can itself communicate with the existing database of seizure data to define seizure detection features and algorithms. For example, and referring to FIG. 1B, features and algorithms can be defined via method 300 and implementation using circuitry 106.

Method 300 generally includes a descriptive analysis 302. In an embodiment, descriptive analysis 302 is generally utilized to understand the seizure data and existing patterns within the seizure data. In an embodiment, minimum, maximum, skewness, standard deviation, and kurtosis measurements can be applied. In embodiments, central tendency measurements such as mean, median, and mode can be applied. In embodiments, plot frequency distributions can be applied.

Descriptive analysis 302 can further include data preparation 304. Data preparation 304 can include identifying missing values, identifying mismatched data types, identifying outliers, and identifying features. Data preparation 304 can further include scaling, normalizing, and/or selecting hyperparameters to select or tune an algorithm.

In particular, embodiments can determine the mean, median, etc. of the two sets of signals (seizure, non-seizure) to discover if the signal has stochastic and deterministic components. Embodiments can then observe the variability of the data, and determine if the data follows a normal distribution (by looking at skewness and kurtosis). Such data preparation 304 forms the basis for selecting which features to extract.

More particularly, data preparation 304 can include application of heat maps for visualizing correlations, and/or application of box plots for indicating variability outside the upper and lower quartiles for the two sets (seizure, non-seizure). Embodiments can further include distribution of mean over 1-second and 7-second windows for datasets without seizure compared to the dataset at seizure onset.

In one embodiment, data preparation 304 includes:
Substitution of missing values with the mean
Visualization of outliers and substitution with mean.
Application of mean max scaler
Testing the data is normal using r library qqnorm and
    qqline. A 45 degree shows that pass for normalized test
Conversion time domain to frequency domain
Definition of the frequency bins
Computation of fast Fourier transform (FFT)
Visualization of frequency vs. power for all observations In one embodiment, referring to FIG. 4A, an illustration of example descriptive statistics and the corresponding example seizure data samples for those statistics is depicted in accordance with examples of the present disclosure. For example, referring to the illustrated descriptive statistics, various seizure and non-seizure data for mean, median, mean absolute deviation, standard deviation, skewness, and Kurtosis are illustrated.

Figures 4A, 4B:
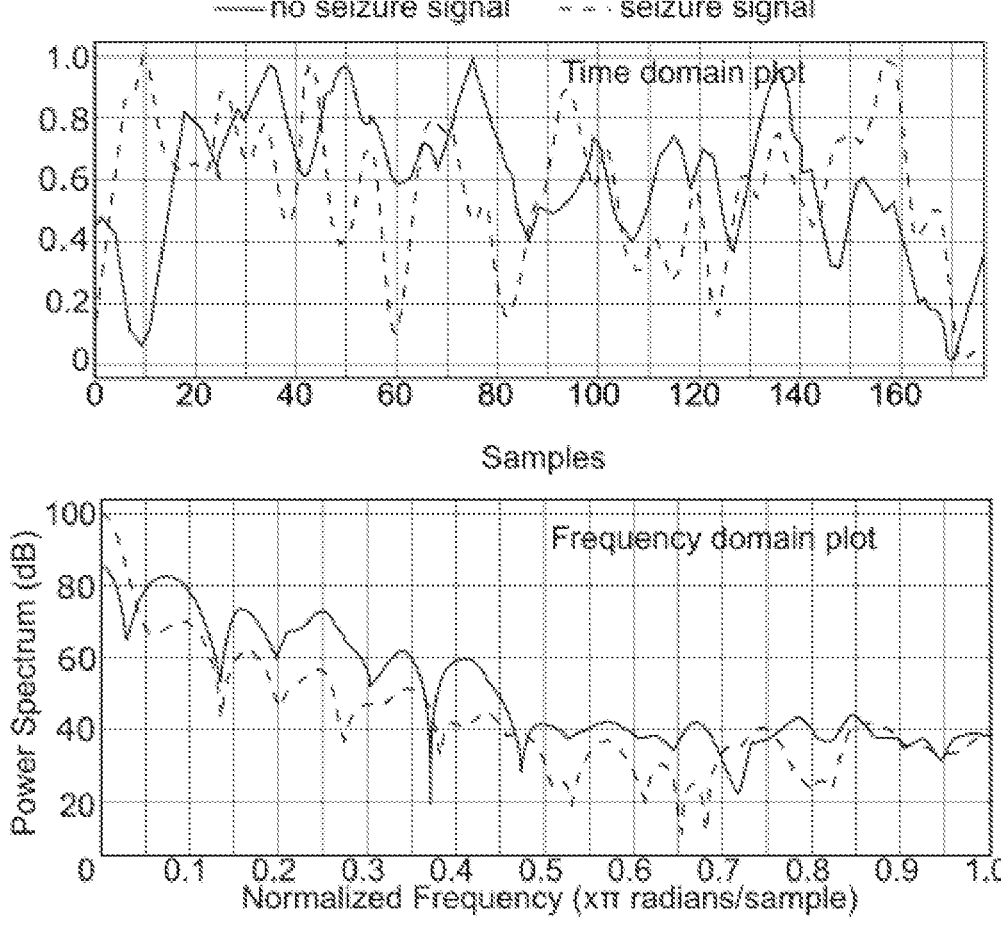
FIG. 4A is an illustration of example descriptive statistics and the corresponding example seizure data samples for those statistics in accordance with examples of the present disclosure.
FIG. 4B is an illustration of graphs of example seizure data accordance with examples of the present disclosure.

Referring to FIG. 4B, an illustration of graphs of example seizure data are depicted in accordance with examples of the present disclosure. Non-seizure data is depicted in dark data points and seizure data is depicted in light data points. The seizure data and non-seizure data is graphed concurrently in the time and frequency domain to demonstrate signal distinction.

A time domain plot is depicted in the upper graph of electrical activity vs. samples. A frequency domain plot of the same data is depicted in the lower graph as power spectrum (dB) vs. normalized frequency (i.e. radians/sample). Accordingly, the inventors have discovered the power spectrum frequency domain plot is where the seizure data begins to have meaning.

Figure 4C:
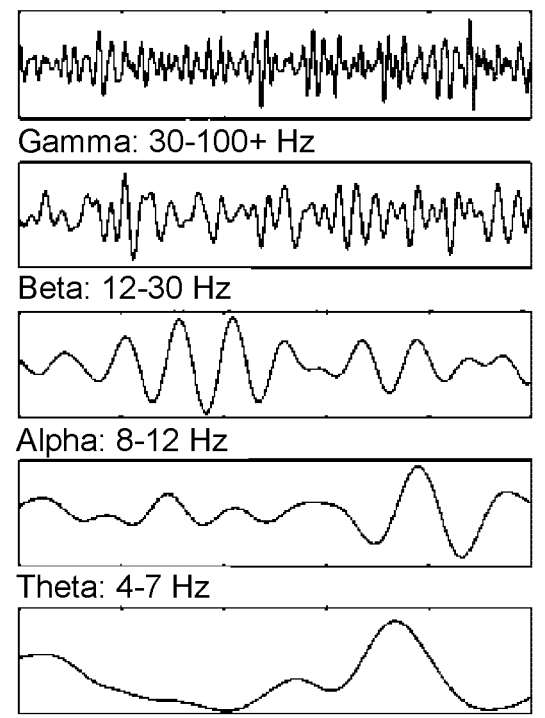
FIG. 4C is an illustration of various EEG bands, which are utilized accordance with examples of the present disclosure.

Referring to FIG. 4C, an illustration of various EEG bands is depicted, which are utilized in accordance with examples of the present disclosure. For example, one of ordinary skill in the art will readily appreciate that different EEG bands can reflect different biological characteristics. Accordingly, features can be selected primarily based on the power spectral density of the EEG, and in the following ranges:
20-100 Hz
12-30 Hz
8-12 Hz
4-7 Hz
0-4 Hz
As described herein, time series measurements can be incorporated in seizure detection algorithms. In general, each set represents a different spectrum related to a particular mental state or even motor coordination in the brain.

Figure 4D:
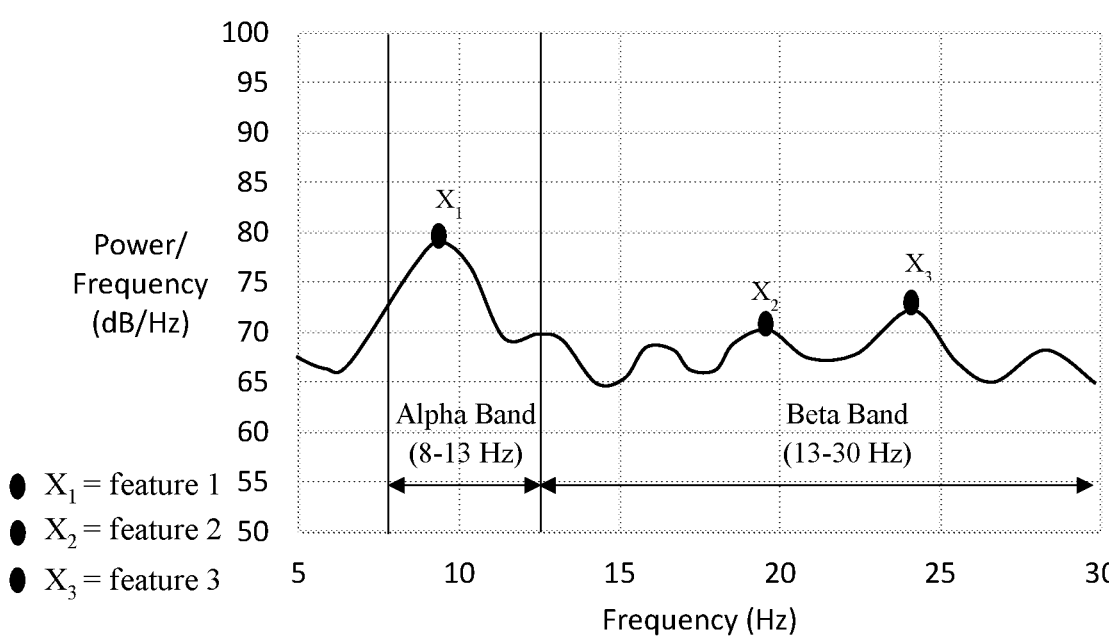
FIG. 4D is a graph of example features selected from the EEG bands of FIG. 4C in accordance with examples of the present disclosure.

In a particular embodiment, extracted features can include:
Alpha band: the maximum of the power spectrum
    between 7 and 4 Hz.
Beta band 1: the maximum of the power spectrum
    between 13 and 20 Hz.
Beta band 2: the maximum of the power spectrum
    between 20 and 30 Hz.
Delta band: the maximum of the power spectrum between
    0 and 4 Hz.
Theta band: the maximum of the power spectrum between
    4 and 7 Hz.
Gamma band: the maximum of the power spectrum
    between 30 and 100 Hz.
Referring to FIG. 4D, a graph of example features selected from the EEG bands of FIG. 4C is depicted in accordance with examples of the present disclosure. FIG. 4D is adapted from information provided in a publication by Nursel Ozmen N, Gumusel L, Yang Y entitled, "A Biologically Inspired Approach to Frequency Domain Feature Extraction for EEG Classification." Compute Math Methods Med. 2018 Jan. 23; 2018:9890132. doi: 10.1155/2018/9890132. PMID: 29796060.

For example, feature 1 is selected in the Alpha band, and feature 2 and feature 3 are selected in the Beta band. In embodiments, Beta band features are highly useful. Accordingly, embodiments can include time series features using a biologically inspired feature set.

As illustrated, data preparation 304 can facilitate unsupervised learning 306, such as in the form of clustering 308. For example, unsupervised learning 306 can utilize kMeans clustering. Though not depicted, unsupervised learning 306 can further include implementation using a neural network.

Data preparation 304 can further facilitate supervised learning 310, such as classification 312 and/or regression 314. For example, supervised learning 310 can utilize a support vector machine (SVM) configured with classification algorithms for two-group classification. Supervised learning 310 can further utilize nearest neighbor algorithms. In embodiments, the output of supervised learning 310 results in two classes: "seizure present" or "seizure not present."

In a particular embodiment, machine learning feature selection can utilize a neighborhood component analysis (NCA). NCA is a non-parametric method for automatically selecting features from the data set. In preparation for using the NCA method, the model can be tuned by using a regularization parameter (lambda) that influences the weightage of each feature and produces the least amount of classification loss. Classification loss functions measure the predictive inaccuracy of classification models. SVM exhibits a lower loss and therefore indicative of a better predictive model.

After using a technique called 5 fold cross validation (using collected data to test and train the model), a loss of 0.0491 was computed. The machine learning algorithm is accordingly tuned with a lambda of 0.0491 and a tolerance of 0.1. A support vector machine classifier was then employed using such hyperparameter optimizations. Accordingly, numerous features can be automatically extracted from the algorithm, leading to a separation that could be graphed in a scatter plot format. One skilled in the art will readily appreciate such techniques for feature extraction.

Figure 4E:
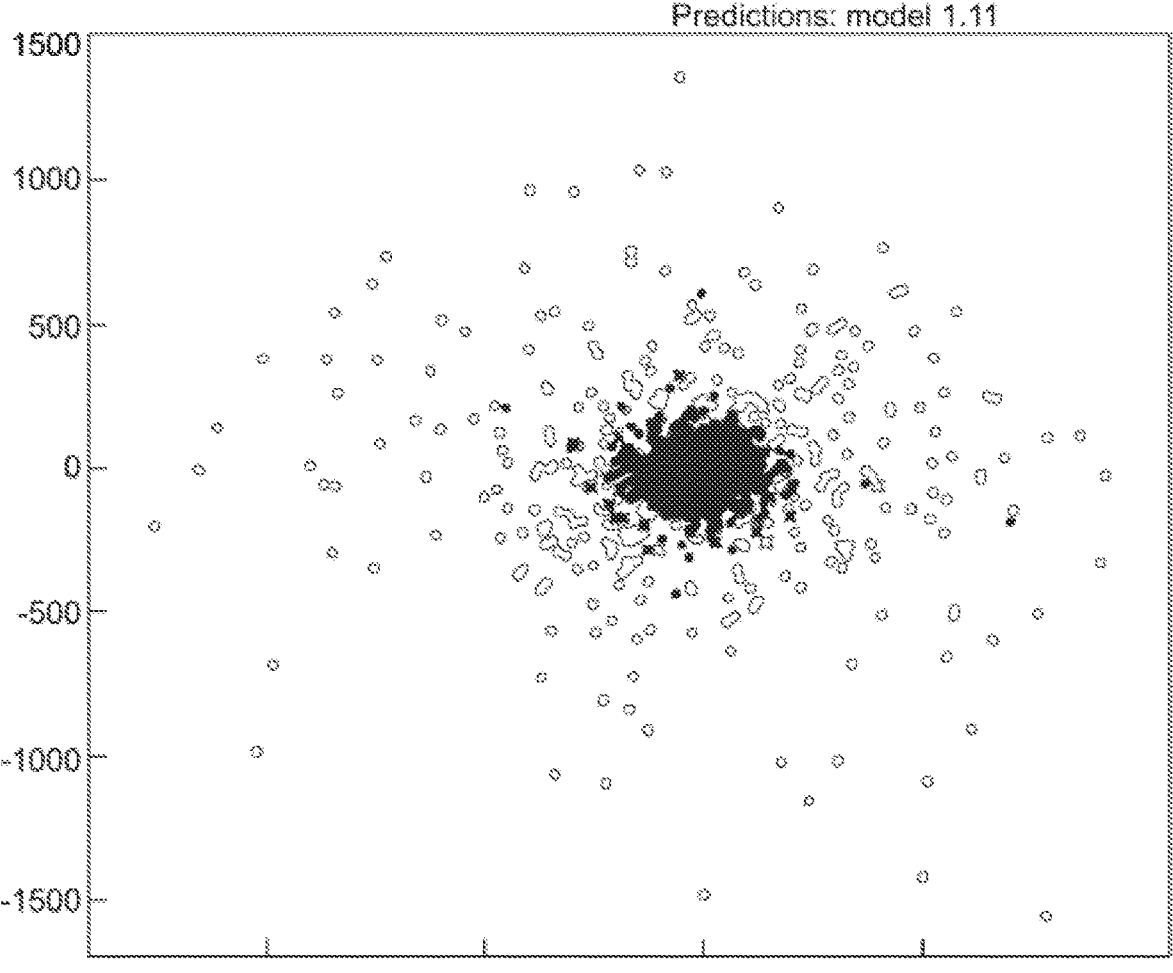
FIG. 4E is a graph of non-seizure data and seizure data clustering, in accordance with examples of the present disclosure.

In one embodiment, referring to FIG. 4E, a graph of non-seizure data and seizure data clustering is illustrated, in accordance with examples of the present disclosure. The graph in FIG. 4E demonstrates the separation in two types of brain signals based on embodiments of algorithmic discrimination techniques.

In particular, an SVM technique demonstrates clustering of non-seizure data (dark data points) vs. seizure data (light data points). Accordingly, an accuracy of 97.2% is achieved. In embodiments, ensemble techniques using bagged trees or a support vector machine using a Gaussian technique can be utilized. One skilled in the art will readily appreciate such techniques for feature extraction. Embodiments can thus incorporate machine learning-defined features.

Accordingly, embodiments described herein utilize frequency discrimination, time series features, and machine learning clustering algorithms to distinguish between the EEG signal of those experiencing a seizure compared to those who are not experiencing a seizure.

Figure 5:
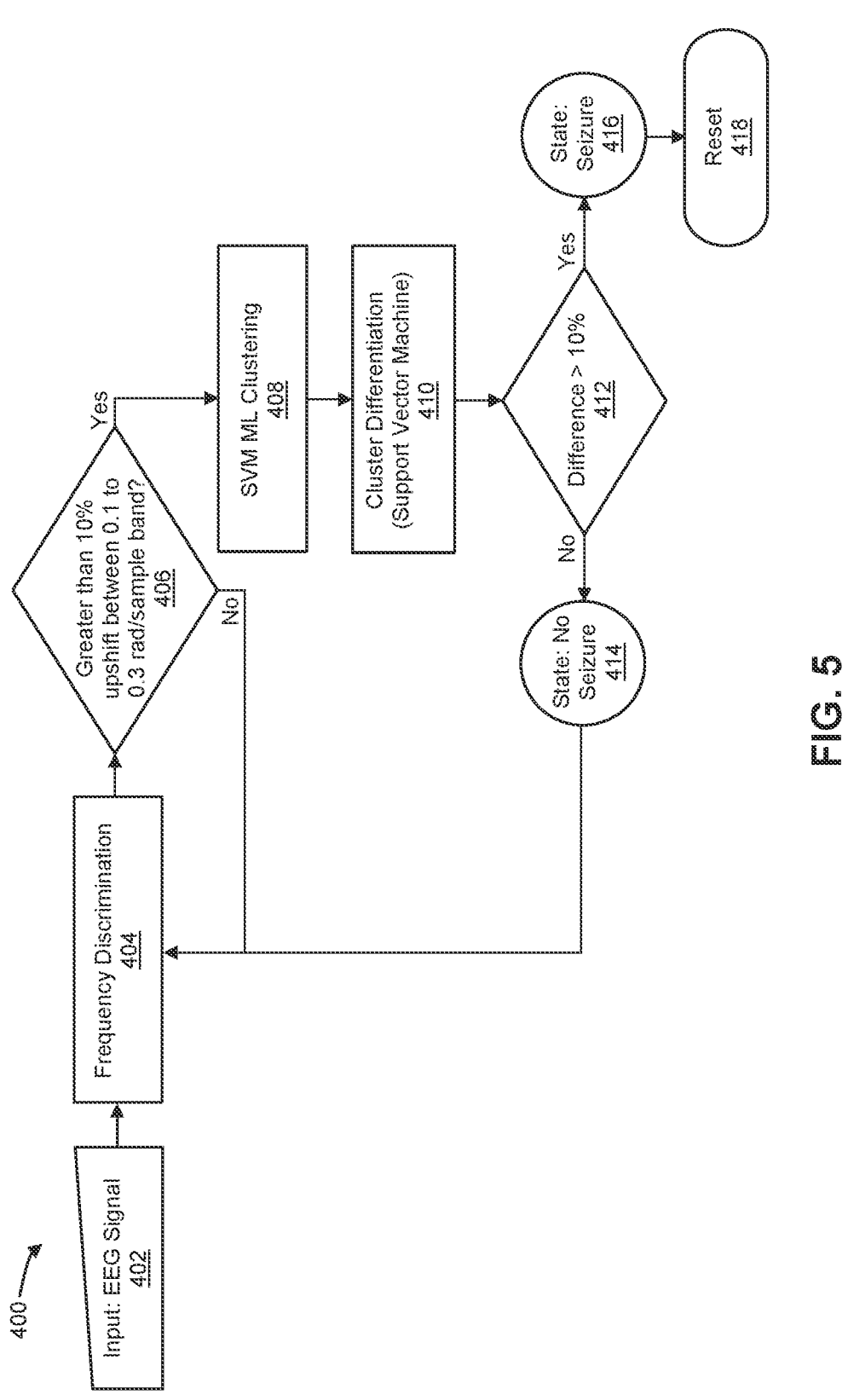
FIG. 5 is a flowchart illustrating an example technique for determining a seizure in accordance with examples of the present disclosure.

Referring to FIG. 5, a flowchart illustrating an example method 400 for determining a seizure is depicted, in accordance with examples of the present disclosure. As will be readily appreciated, method 400 can be implemented by systems 100 and/or 200. Reference is made herein to system 100 and detection device 102.

Method 400 comprises receiving an input signal at 402, such as an EEG signal. For example, detection device 102 can utilize sensing circuitry 108 to receive an input signal from patient 104.

In an embodiment, sensing circuitry 108 can undersample the input signal. For example, typical EEG signals are provided at 1000 Hz. In embodiments, sensing circuitry 108 can utilize signals at 256 Hz or any relatively "lower" rate. In one embodiment, sensing circuitry 108 itself at sample at 256 Hz. In another embodiment, sensing circuitry 108 can sample at a relatively higher rate, but the hardware or software registers which are populated as a result of the sampling are not read at the higher rate, but at the relatively lower 256 rate (e.g. 256 Hz).

In an embodiment, such relatively less-frequent sampling preserves detection device 102 battery life. More particularly, the lesser a frequency on which the sensing circuitry 108 telemetry can operate, the fewer data processing resources are required.

At 404, frequency discrimination is applied to the received signal. Referring also to 406, an evaluation of the frequency-discriminated data is made at an initial thresholding frequency band. As illustrated in FIG. 5, if a greater than 10% upshift between 0.1 to 0.3 rad/sample band is not satisfied, method 400 returns to frequency discrimination application at 404. However, if a greater than 10% upshift between 0.1 to 0.3 rad/sample band is satisfied, method 400 proceeds to subsequent analysis operations. One skilled in the art will readily appreciate that different criteria for the thresholding frequency band can be used.

For example, a Fourier transform can be applied to EEG data to obtain the power spectrum (e.g. the Frequency domain plot of FIG. 4B). The data can be graphed with the x axis as the normalized frequency in units of pi radians per sample, and the y axis as power spectrum in units of dB. When this transform is done for a normal individual compared to one experiencing a seizure, a good separation of the two signals can be observed, especially between the 0.1 to 0.3 pi radians per sample band. The inventors have discovered through observations of multiple epochs of data, that a 10% shift in power spectrum (i.e. a 10% upshift in dB) is a discernable difference between a normal signal and seizure signal. Accordingly, such thresholding reflects a good initial decision point for demonstrating seizure. In certain embodiments, such a shift can be observed with only 1 second of recorded data.

In embodiments, an efficient implementation of such an algorithm can include an n−1 filter in order to approximate the first derivative of the time domain signal (e.g. frequency). This is efficient in implementing low current drain on a detection device because the power spectrum calculation (n−1) is the least amount of integrated circuit flips and flops to estimate the first derivative of the time domain signal, thus saving on device current usage.

At 408, SVM machine learning clustering is applied. For example, processing circuitry 106 can apply a clustering algorithm to the frequency-discriminated data.

In an embodiment, the clustering of machine learning technique SVM can be utilized to differentiate non-seizure data from seizure data. More particularly, the two sets of data—normal EEG and seizure EEG—can be described using 1) feature extraction with time series features (e.g. at 406) and/or with 2) abstractions and computer-recognized distinctions (e.g. automatically-generated features). Each one of these features can be used to describe the two sets of data. In certain embodiments, SVM ML clustering at 408 uses all of the machine described features and time series described features.

For example, at 410, a cluster differentiation is made. In an embodiment, processing circuitry 106 can apply an appropriate cluster differentiator. A hyperplane can be utilized to effectively draw a line of separation between the two types of EEG signals. In embodiments, the two groups of data can be distinguished by point-distance methods to describe the clustering because the separation is good (97% accuracy).

At 412, if the difference resulting from the cluster differentiation is greater than a given threshold, a "no seizure" state is determined at 414. At 412, if the difference resulting from the cluster differentiation is less than a given threshold, a "seizure" state is determined at 416. For example, processing circuitry 106 can determine "no seizure" or "seizure" states. As illustrated, the given threshold for the difference resulting from the cluster differentiation is 10%, but one skilled in the art will readily appreciate that other threshold values can be used. Should a "seizure" state be determined, alerting circuitry 112 can appropriately alert a user of a detected seizure.

Embodiments therefore utilize frequency discrimination and machine learning techniques to determine seizure or non-seizure states. In contrast to traditional classification schemes, which typically rely solely on a Euclidian analysis, embodiments utilize DSP, time domain, and frequency domain discrimination techniques.

At 418, method 400 can reset such that detection device 102 is re-instantiated and new input can be received at 402.

Figure 6:
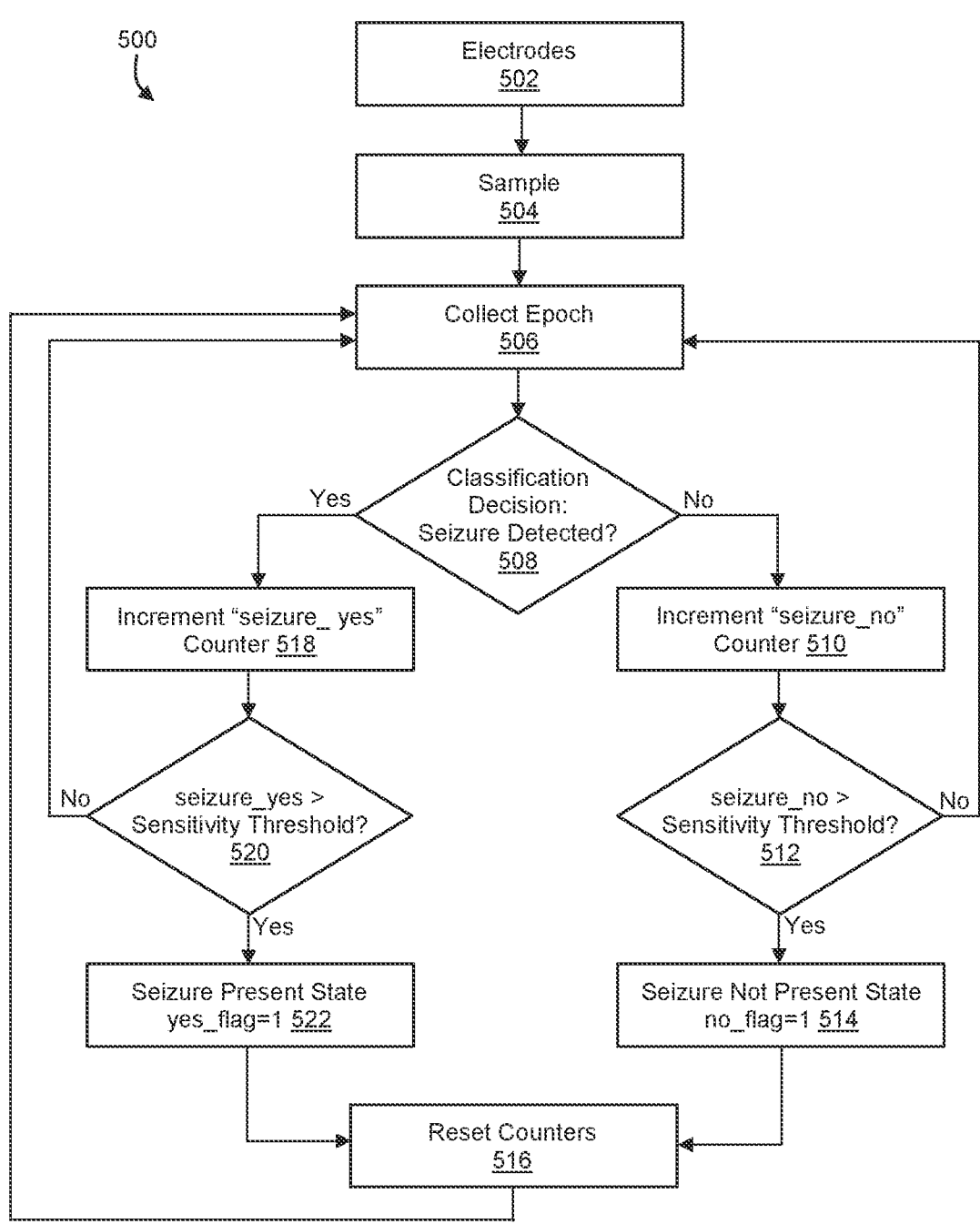
FIG. 6 is a flowchart illustrating an example technique for determining a seizure in accordance with examples of the present disclosure.

In an embodiment, referring to FIG. 6, a flowchart illustrating an example method 500 for determining a seizure is depicted, in accordance with examples of the present disclosure. As will be readily appreciated, method 500 can be implemented by systems 100 and/or 200. Reference is made herein to system 100 and detection device 102.

At 502, a seizure detection device having electrodes, such as detection device 102 is provided. For example, deep brain stimulation and recording leads or scalp-based electrodes can be utilized.

At 504, a data is sampled from the electrodes of detection device 102. In an embodiment, data can be sampled at 256 Hz.

At 506, an epoch of data is collected. For example, a collection window can be pre-defined to collect a certain epoch of data. In an embodiment, the collection window defines a 1 second epoch of data. While other collection windows can be utilized, embodiments described herein only need 1 second of data due to the very fast learning algorithms for seizure detection.

At 508, a "seizure" or "no seizure" classification decision is determined for the collected epoch of data. A binary classifier forces a decision to seizure present/not present states. For example, method 400 can be implemented at 508 to generate the binary output classification.

At 510, referring first to the case in which the classification detection is "no seizure" detected, a counter defined as seizure_no is incremented. At 512, the seizure_no counter is evaluated against a no-count sensitivity threshold. If the seizure_no counter is less than the no-count sensitivity threshold, method 500 returns to data collection at 506. At 514, if the seizure_no counter is greater than the no-count sensitivity threshold, a seizure not present state is indicated by setting no_flag to 1. At 516, the seizure_no counter is reset.

At 518, referring second to the case in which the classification detection is "seizure" detected, a counter defined as seizure_yes is incremented. At 520, the seizure_yes counter is evaluated against a yes-count sensitivity threshold. If the seizure_yes counter is less than the yes-count sensitivity threshold, method 500 returns to data collection at 506. At 522, if the seizure_yes counter is greater than the yes-count sensitivity threshold, a seizure present state is indicated by setting yes_flag to 1. At 516, the seizure_yes counter is reset.

In an embodiment, the sensitivity of the algorithm can be changed by altering the sensitivity thresholds for the number of epochs required to select a state. The higher the figure, the less sensitive it is. Default can be set at "2." In embodiments, the sensitivity thresholds can be the same for both the seizure_yes counter as well as the seizure_no counter. In other embodiments, the sensitivity threshold for the seizure_yes counter can be different from the sensitivity threshold for the seizure_no counter.

Embodiments allow for the selection of higher or lower sensitivity thresholds. For example, sensitivity thresholds can be selected based on lead placement. The placement of leads can result in slightly different amplitudes (i.e. different vectors). Being able to select different amplitudes can help with this sensitivity.

In another example, sensitivity thresholds can be selected based on the type of lead used. DBS, scalp, or subcutaneous leads can all include a particular form of signal attenuation. Being able to select different amplitudes can help with this attenuation.

Figure 7:
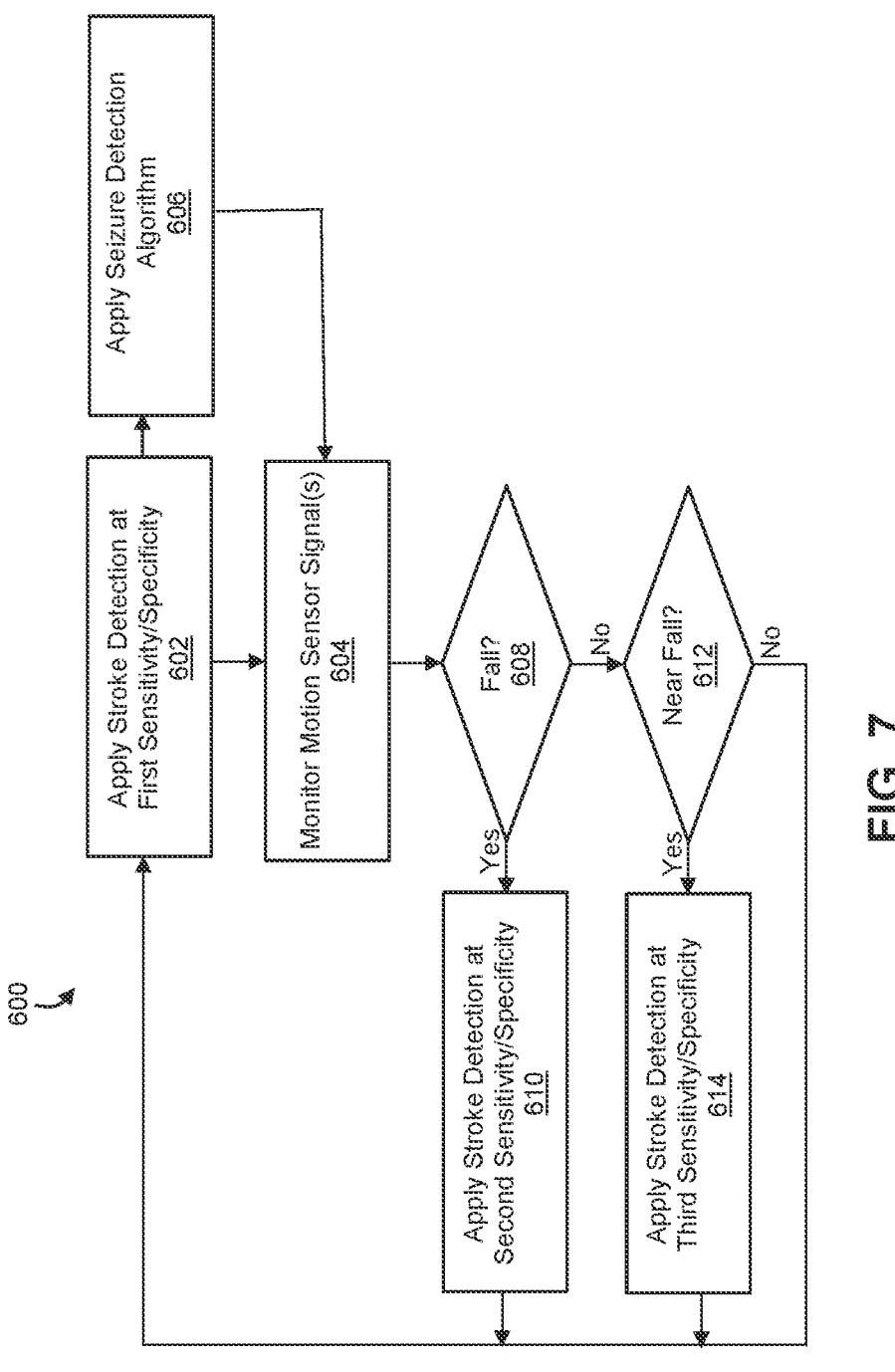
FIG. 7 is a flowchart illustrating an example technique for determining a stroke using embodiments for determining a seizure in accordance with examples of the present disclosure.

Referring to FIG. 7, a flowchart illustrating an example method 600 for determining a stroke using embodiments for determining a seizure in accordance with examples of the present disclosure. In patients experiencing a stroke, there is often a correlation with seizure. Accordingly, seizure detection can be an additional element of stroke detection. The risk of seizures is significant in patients who have experienced stroke. Some studies indicate that incidence of post-stroke seizures can be between 2-20%, as described in Curr Neurol Neurosci Rep.; 19 (7): 37. doi: 10.1007/s11910-019-0957-4, PMID 31134438).

Method 600 generally comprises applying stroke detection at a first sensitivity or specificity at 602. The stroke detection algorithm can have an associated sensitivity and specificity, which can be affected by values of one or more thresholds, such as a probability threshold for determining that stroke is occurring or sufficiently likely to occur.

In one embodiment, referring to 604, one or more motion signals from various motion sensor(s) can be monitored from 602. In another embodiment, referring to 606, the seizure detection algorithms described herein can be applied, thereby increasing the likelihood of positive stroke identification. From 606, motion signals can be monitored at 604.

At 608, based on the one or more motion signals and optionally, output of the seizure detection algorithm, method 600 determines whether the patient has fallen. For example, if the seizure detection algorithm determines a seizure, the patient may be more likely to be experiencing a fall. If the patient has fallen, method 600 can apply stroke detection at a second sensitivity or specificity at 610. 610 can have a higher sensitivity and lower specificity than 602. Embodiments can adjust the sensitivity or specificity by adjusting parameters of the algorithm, such as lowing a probability threshold for stroke.

At 612, if method 600 does not determine that the patient has fallen (No from 612), method 600 may determine whether the patient has experienced a near fall based on the one or more motion signals and optionally, output of the seizure detection algorithm. For example, if the seizure detection algorithm determines a seizure, the patient may be more likely to be experiencing a near fall. If method 600 determines that the patient has experienced a near fall, method 600 can apply the stroke detection algorithm at a third sensitivity or specificity. In an embodiment, the third sensitivity or specificity can be between the first and second sensitivity and specificity. If method 600 does not determine that the patient has experienced a near fall (No from 612), method 600 returns to 602 to apply the algorithm at the first sensitivity or specificity.

In embodiments, the timing of a seizure in relation to the onset of the stroke is important for determining the risk of developing epilepsy. In this embodiment, the onset of each event (stroke and seizure) can be logged in order for a clinician to determine the risk of stroke.

Stroke storm (strokes/second) is also an important for determining the risk of developing epilepsy and can further be included in method 600.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

FURTHER EXAMPLES

1. A seizure detection device comprising:

sensing circuitry comprising at least one electrode configured to generate electroencephalogram (EEG) signal data; and processing circuitry configured to:

receive the EEG signal data according to a collection window epoch, generate a power spectral density estimation of the EEG signal data, determine whether a shift in power spectrum has occurred for a selected band based on the power spectral density estimation, when the shift in power spectrum has occurred for the selected band:

apply a machine-learning clustering to the EEG signal data to generate a clustered data set based on at least a plurality of time-series features and a plurality of machine learning-defined features, apply a cluster differentiator to the clustered data set to separate the EEG signal data, indicate a seizure state when the EEG signal data is greater than a differentiator threshold, and indicate a non-seizure state when the EEG signal data is less than the differentiator threshold.

2. The seizure detection device of example 1, wherein the collection window epoch is 1 second.

3. The seizure detection device of example 1, wherein the selected band is 0.1 to 0.3 pi radians per sample and the shift is a 10% upshift in dB.

4. The seizure detection device of example 1, wherein the power spectral density estimation includes an n−1 filter to approximate the first derivative of a time domain signal of the EEG signal data 5. The seizure detection device of example 1, wherein the cluster differentiator is a hyperplane.

6. The seizure detection device of example 1, wherein the processing circuitry is further is configured to:

when the seizure state is indicated, increment a seizure state counter, compare the seizure state counter against a seizure sensitivity threshold, and indicate a seizure present state when the seizure state counter is greater than the seizure sensitivity threshold, wherein the seizure detection device further comprises alerting circuity configured to alert a user including when the processing circuitry indicates the seizure present state.

7. The seizure detection device of example 1, wherein the processing circuitry is further is configured to:

when the non-seizure state is indicated, increment a non-seizure state counter, compare the non-seizure state counter against a non-seizure sensitivity threshold, and indicate a non-seizure present state when the non-seizure state counter is greater than the non-seizure sensitivity threshold, wherein the seizure detection device further comprises alerting circuity configured to alert a user including when the processing circuitry indicates the non-seizure present state.

8. The seizure detection device of example 1, wherein the seizure detection device is wearable by a patient, and wherein the at least one electrode is a wearable sensor.

9. The seizure detection device of example 8, wherein the at least one electrode is operably coupleable to skin of the patient by an adhesive element, and wherein the seizure detection device further comprises a wearable band to further secure the at least one electrode to the skin of the patient.

10. A method of detecting a seizure with a seizure detection device, the seizure detection device including sensing circuitry comprising at least one electrode configured to generate electroencephalogram (EEG) signal data, the method comprising:

receiving the EEG signal data according to a collection window epoch;

generating a power spectral density estimation of the EEG signal data;

determining whether a shift in power spectrum has occurred for a selected band based on the power spectral density estimation;

when the shift in power spectrum has occurred for the selected band:

applying a machine-learning clustering to the EEG signal data to generate a clustered data set based on at least a plurality of time-series features and a plurality of machine learning-defined features, applying a cluster differentiator to the clustered data set to separate the EEG signal data, indicating a seizure state when the EEG signal data is greater than a differentiator threshold, and indicating a non-seizure state when the EEG signal data is less than the differentiator threshold.

11. The method of example 10, wherein the collection window epoch is 1 second.

12. The method of example 10, wherein the selected band is 0.1 to 0.3 pi radians per sample and the shift is a 10% upshift in dB.

13. The method of example 10, wherein the power spectral density estimation includes an n−1 filter to approximate the first derivative of a time domain signal of the EEG signal data 14. The method of example 10, wherein the cluster differentiator is a hyperplane.

15. The method of example 10, further comprising:

when the seizure state is indicated, incrementing a seizure state counter, comparing the seizure state counter against a seizure sensitivity threshold, and indicating a seizure present state when the seizure state counter is greater than the seizure sensitivity threshold, alerting a user including when the seizure present state is indicated.

16. The method of example 10, further comprising:

when the non-seizure state is indicated, incrementing a non-seizure state counter, comparing the non-seizure state counter against a non-seizure sensitivity threshold, and indicating a non-seizure present state when the non-seizure state counter is greater than the non-seizure sensitivity threshold, alerting a user including the non-seizure present state is indicated.

17. The method of example 10, wherein the seizure detection device is wearable by a patient, and wherein the at least one electrode is a wearable sensor.

18. The method of example 17, wherein the at least one electrode is operably coupleable to skin of the patient by an adhesive element, and wherein method further comprises a using a wearable band to further secure the at least one electrode to the skin of the patient.

What is claimed is:

1. A seizure detection device comprising:

sensing circuitry comprising at least one electrode configured to generate electroencephalogram (EEG) signal data; and processing circuitry configured to:

receive the EEG signal data according to a collection window epoch, generate a power spectral density estimation of the EEG signal data,

determine whether a shift in power spectrum has occurred for a selected band based on the power spectral density estimation, when the shift in power spectrum has occurred for the selected band:

apply a machine-learning clustering to the EEG signal data to generate a clustered data set based on at least a plurality of time-series features and a plurality of machine learning-defined features, apply a cluster differentiator to the clustered data set to separate the EEG signal data, indicate a seizure state when the EEG signal data is greater than a differentiator threshold, and indicate a non-seizure state when the EEG signal data is less than the differentiator threshold.

2. The seizure detection device of claim 1, wherein the collection window epoch is 1 second.

3. The seizure detection device of claim 1, wherein the EEG signal data is sampled at a rate lower than 1000 Hz.

4. The seizure detection device of claim 1, wherein the EEG signal data is sampled at a rate of 256 Hz.

5. The seizure detection device of claim 1, wherein the selected band is 0.1 to 0.3 pi radians per sample and the shift is a 10% upshift in dB.

6. The seizure detection device of claim 1, wherein the power spectral density estimation includes an n−1 filter to approximate the first derivative of a time domain signal of the EEG signal data.

7. The seizure detection device of claim 1, wherein the cluster differentiator is a hyperplane.

8. The seizure detection device of claim 1, wherein the processing circuitry is further configured to:

when the seizure state is indicated, increment a seizure state counter, compare the seizure state counter against a seizure sensitivity threshold, and indicate a seizure present state when the seizure state counter is greater than the seizure sensitivity threshold, wherein the seizure detection device further comprises alerting circuitry configured to alert a user including when the processing circuitry indicates the seizure present state.

9. The seizure detection device of claim 1, wherein the processing circuitry is further configured to:

when the non-seizure state is indicated, increment a non-seizure state counter, compare the non-seizure state counter against a non-seizure sensitivity threshold, and indicate a non-seizure present state when the non-seizure state counter is greater than the non-seizure sensitivity threshold, wherein the seizure detection device further comprises alerting circuitry configured to alert a user including when the processing circuitry indicates the non-seizure present state.

10. The seizure detection device of claim 1, wherein the seizure detection device is wearable by a patient, and wherein the at least one electrode is a wearable sensor.

11. The seizure detection device of claim 10, wherein the at least one electrode is operably coupleable to skin of the patient by an adhesive element, and wherein the seizure detection device further comprises a wearable band to further secure the at least one electrode to the skin of the patient.

12. A method of detecting a seizure with a seizure detection device, the seizure detection device including sensing circuitry comprising at least one electrode configured to generate electroencephalogram (EEG) signal data, the method comprising:

receiving the EEG signal data according to a collection window epoch;

generating a power spectral density estimation of the EEG signal data;

determining whether a shift in power spectrum has occurred for a selected band based on the power spectral density estimation;

when the shift in power spectrum has occurred for the selected band:

applying a machine-learning clustering to the EEG signal data to generate a clustered data set based on at least a plurality of time-series features and a plurality of machine learning-defined features, applying a cluster differentiator to the clustered data set to separate the EEG signal data, indicating a seizure state when the EEG signal data is greater than a differentiator threshold, and indicating a non-seizure state when the EEG signal data is less than the differentiator threshold.

13. The method of claim 12, wherein the collection window epoch is 1 second.

14. The method of claim 12, wherein the selected band is 0.1 to 0.3 pi radians per sample and the shift is a 10% upshift in dB.

15. The method of claim 12, wherein the power spectral density estimation includes an n−1 filter to approximate the first derivative of a time domain signal of the EEG signal data.

16. The method of claim 12, wherein the cluster differentiator is a hyperplane.

17. The method of claim 12, further comprising:

when the seizure state is indicated, incrementing a seizure state counter, comparing the seizure state counter against a seizure sensitivity threshold, and indicating a seizure present state when the seizure state counter is greater than the seizure sensitivity threshold, alerting a user including when the seizure present state is indicated.

18. The method of claim 12, further comprising:

when the non-seizure state is indicated, incrementing a non-seizure state counter, comparing the non-seizure state counter against a non-seizure sensitivity threshold, and indicating a non-seizure present state when the non-seizure state counter is greater than the non-seizure sensitivity threshold, alerting a user including when the non-seizure present state is indicated.

19. The method of claim 12, wherein the seizure detection device is wearable by a patient, and wherein the at least one electrode is a wearable sensor.

20. The method of claim 19, wherein the at least one electrode is operably coupleable to skin of the patient by an adhesive element, and wherein the method further comprises using a wearable band to further secure the at least one electrode to the skin of the patient.

\* \* \* \* \*